(12) United States Patent
Lassota et al.

(10) Patent No.: US 6,774,143 B1
(45) Date of Patent: Aug. 10, 2004

(54) METHOD FOR TREATING CELLS RESISTANT TO ANTINEOPLASTIC AGENTS

(75) Inventors: Peter Lassota, Succasunna, NJ (US); Christopher Turchik Jagoe, Chatham, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/240,645

(22) PCT Filed: Apr. 4, 2000

(86) PCT No.: PCT/US00/08904

§ 371 (c)(1),
(2), (4) Date: Apr. 10, 2003

(87) PCT Pub. No.: WO01/74355

PCT Pub. Date: Oct. 11, 2001

(51) Int. Cl.[7] ............................................. A61K 31/35
(52) U.S. Cl. ........................ 514/460; 514/449; 514/451
(58) Field of Search .............................. 514/431, 460, 514/451, 449

(56) References Cited

FOREIGN PATENT DOCUMENTS

WO          WO 97/20835          6/1997

OTHER PUBLICATIONS

Kowalski et al., Mol. Pharmacol., 52(4), Oct. 1997, pp 613–622.*
Balachandran et al., Anticancer Drugs, 9(1), pp 67–76, 1998.*
Internal Medicine, 4th Edition, Editor–in–Chief Jay Stein, Chapters 71–72, pp. 699–715, 1994.*
Kowalski et al., "The microtuble–stabilizing agent discodermolide competitively inhibits the binding of Paclitaxel (Taxol) to tublin polymers, enhances tubulin nucleation reactions . . . ," Mol. Pharmacol., vol. 52, No. 4, pp. 613–622 (1997).
Balachandran et al., "The potent microtubule–stabilizing agent (+)–discodermolide induces apoptosis in human breast carcinoma cells—preliminary comparisons to paclitaxel," Anti–Cancer Drugs, vol. 9, pp. 67–76 (1998).
Morsman et al., "Taxane chemotherapy and new microtubule–interactive agents," Curr. Opinion Oncol, Endocrin. Metabol. Invest. Drugs, vol. 2, No. 3, pp. 305–311 (2000).
Longley et al., "Increased potency of (+) discodermolide vs. Paclitaxel against multidrug resistant MCF–7/ADR cells," Proc. Am. Assoc. Cancer Res. Annual Meet., No. 41, vol. 41, p. 269 (2000) Abstract Nr. 1716.

Bollag D. M., "Epothilones: novel microtubules–stabilizing agents," Expert Opinion Invest. Drugs, vol. 6, No. 7, pp. 867–873 (1997).
Ter Haar et al., "Taxanes and other microtubule–stabilizing agents," Expert Opinon Ther. Pat., vol. 8, No. 5, pp. 571–586 (1998), Abstract 1998146520.
Fojo et al., "Taxol and other microtubule–interactive agents," Curr. Opinion Oncol. Endocr. Metab. Invest. Drugs, vol. 2, No. 3, 2000, pp. 293–304.
Sorensen et al., "Discodermolide, a potent microtubule stabilizing agents, is not cross–resistant with paclitaxel in–vitro and in–vivo," AACR, vol. 91, p. a3528 (2000)., Abstract #3528.
Balachandran et al., "Increased sensitivity of the antiestrogen–resistant MCF–7/LY2 human breast carcinoma cell line to apoptosis induced by the novel mcirotubule stabilizing agent (+)–discodermolide," Breast Journal, vol. 4, No. 6, pp. 409–419 (1998).
Jordan et al., "Microtubules and actin filaments: dynamic targets for cancer chemotherapy," Curr. Opinion Cell. Biol., vol. 10, No. 1, pp. 123–130 (1998).
Dumontet et al., "Mechanisms of action of and resistance to antitubulin agents: microtubule dynamics, drug transport and cell death," J. Clin. ONcol., vol. 17, No. 3, pp. 1061–1070 (1999).
Balachandran et al. "Effects of the novel mcirotubule stabilizing agents, discodermolide, on the microtubule network, nuclear morphology and viability of breast cancer cells." AACR, vol. 87, p. a2996 (1996) Asbract No. 2996.
Longley et al., "Comparative effects of discodermolide and paclitaxel on induction of apoptosis and perturbation of the cell cycle in various tumor cell lines," AACR, vol. 87, p. a2723, Abstract No. 2723.
Ter Haar et al., "Discodermolide, a cytotoxic marine agent that stabilizes microtubules more potently than taxol," Biochemistry, vol. 35, No. 1, pp. 243–250 (1996).
Jordan et al., "Tublin as a target for anticancer drugs: agents which interact with the mitotic spindle," Medicinal Research Reviews, New York, NY, US, vol. 18, No. 4, pp. 259–296 (1998).

* cited by examiner

*Primary Examiner*—Dwayne Jones
(74) *Attorney, Agent, or Firm*—Lydia McNally; George R. Dohmann

(57) ABSTRACT

The present invention relates to methods for treating multidrug resistant cells, preferably multidrug resistant cancer cells with discodermolide. Discodermolide is found to be effective in limiting the growth of otherwise growth unregulated cells having tubulin mutations and in promoting phosphorylation of the oncogene RAF-1.

51 Claims, 5 Drawing Sheets

Figure 1

Table 1.  Antiproliferative effect of discodermolide against a panel of human carcinoma cell lines

| | IC50 [nM] | | | | | | | | |
|---|---|---|---|---|---|---|---|---|---|
| | Epidermoid | | Lung | | Colon | | Prostate | | Breast | |
| Compound | KB-31 | KB-8511 | A549 | NCI-H460 | HCT-15 | HCT116 | Du 145 | PC-3M | MCF7/ADR | MDA-MB-231 |
| Discodermolide | | | | | | | | | | |
| Sample 1 | 1.5 | 8.9 | 3.5 | 2.1 | 7.3 | 3.8 | 12.0 | 14.7 | 228 | 2.5 |
| Sample 2 | 2.4 | 8.4 | 7.8 | 3.5 | 9.4 | 5.8 | 8.3 | 32.9 | 202 | 6.1 |
| Mean | 2.0 | 8.7 | 5.6 | 2.8 | 8.4 | 4.8 | 10.7 | 23.8 | 215 | 4.3 |
| Paclitaxel | | | | | | | | | | |
| n | 17 | 20 | 8 | 9 | 9 | 10 | 9 | 9 | 5 | 7 |
| Mean ± SEM | 1.4 ± 0.2 | 361 ± 87 | 2.3 ± 0.8 | 3.9 ± 0.5 | 121 ± 13 | 1.7 ± 0.3 | 2.5 ± 0.2 | 2.9 ± 1.1 | 7737 ± 1408 | 1.0 ± 0.2 |

METHOD FOR TREATING CELLS RESISTANT TO ANTINEOPLASTIC AGENTS

BACKGROUND OF THE INVENTION

The present invention relates to methods for treating cells resistant to neoplastic agents. Although there are now a number of cytotoxic agents that help to produce a positive outcome in cancer patient therapy, many cancer cells develop resistance or are resistant to the neoplastic agents currently of choice for chemotherapeutic treatment. The development of drug resistance substantially compromises the efficacy of cancer therapy.

Multidrug resistance cells are one example of cells that are resistant to antineoplastic agents. In this case, the cells are resistant to more than one antineoplastic agent. Multidrug resistance is a well-defined phenomenon. Often cancer cells that become resistant to one class of anticancer drugs (i.e., Vinca alkaloids, anthracyclines, taxanes, including paclitaxel, epipodophyllotoxins, and the like) also demonstrate resistance to other anticancer drugs. Development of multidrug resistance creates a significant impediment in the generation of positive outcomes for many cancer patients. Multidrug resistant agents have a number of general features in common; they are generally lipophili, weakly basic molecules of greater than about 300 daltons or larger molecular weight. Multidrug resistant cells tend to accumulate anticancer drugs at a level lower than cells that are not multidrug resistant (Beck, W T, *Adv. Enzym.o Regul* 1984, 22:207). Accumulation of drug at lower levels has been shown in some models to be associated with an increase in activity or in the amount of a family of transmembrane channel proteins.

An example of transmembrane channel proteins that are capable of decreasing the intercellular concentration of anticancer drugs are the integral membrane proteins P-glycoproteins (Pgp, Endicott J A and Ling, V. *Annu Rev. Biochem.* 1989, 58:137). The proteins appear to bind to antineoplastic agents and release the agents into the extracellular milieu. Expression of the MDR1 cDNA, the DNA encoding Pgp, is sufficient to produce a multidrug resistance phenotype (Gros et al., *Nature* 1986, 323:728). These proteins are present in rodents and in man. Another protein associated with resistance to antineoplastic agents is the multidrug resistance-associated protein (MRP) (Grant C E et al., *Cancer Res.* 1994, 54:357). MRP has been shown to confer multidrug resistance to doxorubicin, vincristine, etoposide and colchicine. For a review of other multidrug resistance associated proteins see "Mechanismns of Drug Resistance" by Beck and Dalton in Cancer: Principles and Practice of Oncology, p. 498–512, eds DeVita et al., Lippincott-Raven, N.Y., 1997.

Elevated levels of Pgp have been observed in a variety of cancers including, but not limited to, Acute Myelogenous Leukemia, Non-Hodgkin's Lymphoma, multiple myeloma as well as in a variety of solid tumors including, but not limited to, cancers of the adrenal, colon, kidney, lung and breast (see Beck and Dalton, supra). Moreover, it is widely recognized that cancers having an origin in a variety of tissues and cells can develop multidrug resistance. Therefore, there is a need to identify and to use compounds that remain toxic to otherwise multidrug resistant cells.

In addition to multidrug resistance, there are other types of resistance to antineoplastic agents that have been observed. These include, for example, resistance to one or more antineoplastic agents as a result of a mutated protein. One example of resistance to antineoplastic agents results from mutations in microtubules or in mutations in tubulin dimers. Cellular resistance to taxanes such as paclitaxel, can be multifactorial. For example, cellular resistance to the taxane family has been associated in some instances with a mutation in the β-tubulin subunit. Again, as in the case of multidrug resistant cells, there is a need for neoplastic agents that remain toxic to taxane-resistant cells.

SUMMARY OF THE INVENTION

The present invention relates to methods for treating cells with discodermolide. In one aspect, the invention relates to methods for treating cells with discodermolide in vivo.

In another aspect of this invention, the invention relates to a method for inhibiting the growth of multidrug resistant cells comprising the step of contacting at least one multidrug resistant cell with a growth-inhibiting amount of discodermolide. In one embodiment the multidrug resistant cell is resistant to taxanes, for example paclitaxel. In another embodiment the multidrug resistant cells are growth inhibited in vivo or in culture. Preferably the cell is from a mammmal and more preferably from a human.

In another aspect of this invention, the invention relates to a method for inhibiting the growth of a cancer cell comprising the steps of: contacting at least one cancer cell with a growth inhibiting amount of discodermolide wherein the cancer cell is resistant to at least one antineoplastic agent. In a preferred embodiment the cancer cell is selected from the group consisting of a leukemia cell, a lymphoma cell and a solid tumor cell. In one embodiment the cancer cell is a multidrug resistant cell. In another embodiment the cell comprises a mutation in β-tubulin and in another embodiment, the cell over-produces glutathione. Preferably the cell is in a mammal.

The invention also relates to a method for promoting apoptosis in a multidrug resistant cell comprising the steps of contacting a multidrug resistant cell with discodermolide; and inducing apoptosis in the cell. In a preferred embodiment the multidrug resistant cell is resistant to paclitaxel. The cell can be a cell in culture or in vivo. Preferably the cell is from a mammal and more preferably from a human.

The invention further relates to a method for inhibiting the growth of cancer cells having a β-tubulin mutation comprising the steps of; contacting at least one cancer cell with a growth inhibiting amount of discodermolide wherein the cell comprises a mutation in the protein β-tubulin; and inhibiting cell division in the cell. In one embodiment the cell is resistant to paclitaxel or to another antineoplastic agent. Preferably growth inhibition occurs in vivo and more preferably growth inhibition occurs in a mammal, preferably a human. The invention also relates to a method for inhibiting growth of a tumor resistant to at least one antineoplastic agent comprising the step of: contacting a tumor with discodermolide wherein the tumor comprises cells resistant to at least one antineoplastic agent. In one embodiment the cells have a mutation in a β-tubulin protein and in another embodiment the cells overproduce glutathione. In yet another embodiment, the cells are multidrug resistant. In a preferred embodiment, the at least one neoplastic agent is paclitaxel. In yet another embodiment the cells comprise raf-1 and wherein raf-1 is phosphorylated in the presence of discodermolide. Preferably the tumor is selected from the group of tumors consisting of lung, prostate, colon, breast, ovarian, kidney, brain, pancreatic esophageal, head and neck, gastric, and liver tumors.

BRIEF DESCRIPTION OF THE FIGURES

FIG. 1 is a table illustrating the antiproliferative activity of discodermolide in various cancer cell lines. Various cancer cell lines were incubated with increasing concentrations of discodermolide or paclitaxel and the IC$_{50}$ for cell proliferation is determined by methylene blue staining.

FIG. 5(a) refers to treatments starting 24 hours after animals were implanted subcutaneously (sc) with hollow fibers (3 fibers/animal, one fiber/each cell line, six animals/compound). Paclitaxel was administered IV, once daily for 5 days at 15 mg/kg. Vehicle control was administered according to the paclitaxel schedule. FIG. 5(b) refers to the identical regimen as 5(a) but here discodermolide rather than paclitaxel was administered iv, as a single 15 mg/kg injection. Vehicle control was administered according to the discodermolide schedule.

Figure 2:
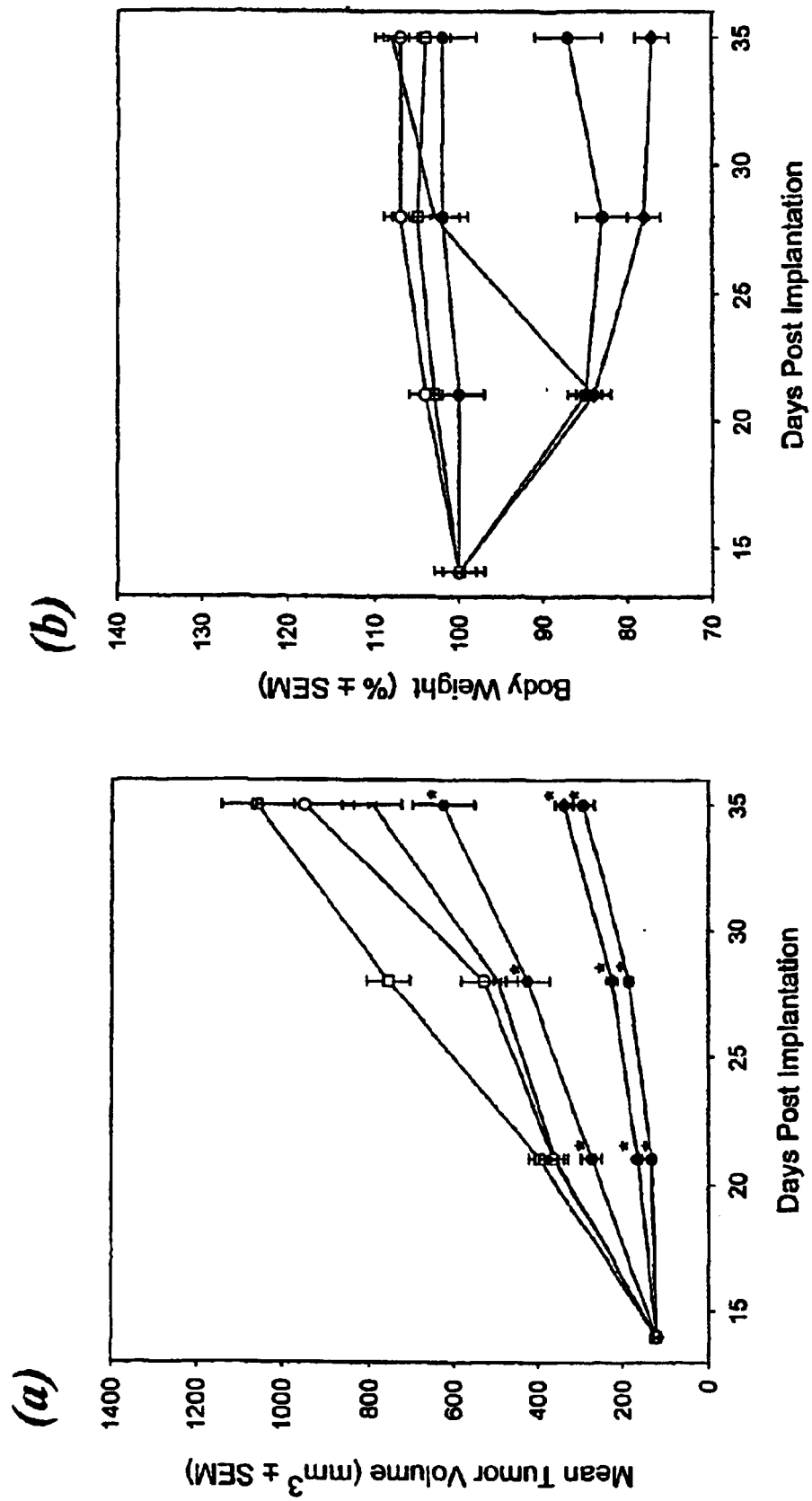
FIG. 2(a) provides the mean tumor volumes and FIG. 2(b) provides mean body weights in a study to assess paclitaxel-resistant (Pgp-1/MRP)-overexpressing human colon tumor xenograft (HCT 15 cells) sensitivity to discodermolide. —□— refers to control solution of 16.7% Crm.-8.3%EtOH/ D5W, iv 1× (d.14); —●— refers to mice receiving discodermolide, iv, 15 mg/kg, 1× (d.14); —◆— refers to mice receiving discodermolide, iv, 7.5 mg/kg, 1× (d.14); —◆— refers to mice receiving discodermolide, iv, 2.5 mg/kg, 1× (d 14); —○— refers to mice receiving 12.5% Crm-12.5% EtOH/D5W, iv, 1×/day (d. 14–16); and —x— refers to mice receiving paclitaxel, iv, 15 mg/kg, 1×/day (d. 14–18).

DESCRIPTION OF THE PREFERRED EMBODIMENTS (+)-Discodermolide (hereinafter referred to as "discodermolide") is a metabolite of the marine sponge *Discodermia dissoluta* (See Gunasekera, et al., *J. Org. Chem.* 55:4912, 1990. Correction: *J. Org. Chem.* 56:1346, 1991).

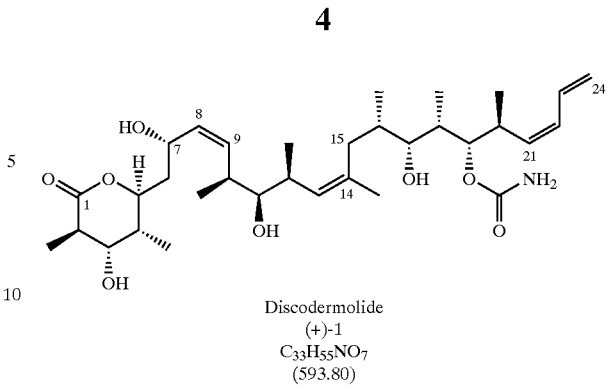

Discodermolide
(+)-1
C$_{33}$H$_{55}$NO$_7$
(593.80)

Despite their different chemical structure, discodermolide is believed to function much the same way as paclitaxel, the active substance in the drug TAXOL. Like paclitaxel, discodermolide acts to inhibit cold-induced depolymerization of purified tubulin, and interferes with microtubule dynamics in cells (ter Haar E, et al., *Biochemistry* 1996; 35:243–50). Proliferating cells treated with the compound are arrested during mitosis, and subsequently undergo apoptosis (Balachandran R, et al., *Anti-Cancer Drugs* 1998; 9:67–76. [Errata *Anti-Cancer Drugs* 1998: 9:369–370]) In a number of studies, discodermolide as been shown to be more potent than paclitaxel in its ability to polymerize purified tubulin and discodermolide binds to tubulin competitively with paclitaxel. Paclitaxel has been shown to disrupt microtubules in tumor cells resulting in cell killing. Thus, investigators are working to confirm the anti-proliferative effects of discodermolide both in vitro and in vivo.

While investigators have demonstrated the superiority of discodermolide as compared with paclitaxel for killing cancer cells, the killing has been performed in culture. The present invention provides data to demonstrate that discodermolide is effective for inhibiting the growth of cancer cells in vivo. In addition, the present invention demonstrates the eficacy of discodermolide in vivo in cells that have demonstrated resistance to at least one antineoplastic agent. The studies described below demonstrate that discodermolide is useful for treating cells both in vivo and in culture and in treating cancer cells where the cancer cells are resistant to at least one antineoplastic agent because, for example, the cancer cells are multidrug resistant; the cancer cells over produce glutathione or because the cancer cells have a mutation in one or more proteins rendering the cells resistant to the antineoplastic agent.

Thus, the term "resistant to at least one neoplastic agent" is used herein to refer to cells, for example, that are multidrug resistant; cells that are resistant to platinum or to other alkylating agents because they tend to over produce glutathione and to cells that have a mutation in one or more cells that render the cells resistant to a particular chemotherapeutic agent. For example, it has been shown that cells resistant to taxanes include a mutation in β-tubulin protein. The present studies support the use of discodermolide in cases where one or more antineoplastic agents have failed to adequately inhibit growth of the cancer cells. The term "resistance" is used herein to refer to cells that are able to survive in the presence of at least one neoplastic agent where the normal cell counterpart (i.e., a growth regulated cell of the same origin) would either show signs of cell toxicity, cell death or cell quiescence (i.e., would not divide).

The term "inhibit the growth of" as used in herein refers to the ability of a particular antineoplastic agent to limit or reduce the growth potential of a cell, preferably a cancer cell. Therefore, a particular antineoplastic agent can inhibit the growth of a cell by reducing the rate at which a particular cell divides, it can cause the cells to remain in a quiescent (i.e., non-dividing state) or it can induce cell cytotoxicity and/or cell death, including apoptosis.

Examples of cancer cells from cancers resistant to at least one antineoplastc agent that can benefit from discodermolide therapy include leukemias and lymphomas, as well as solid tumors such as tumors of the colon, spleen, prostate, liver, lung and breast. FIG. 1 includes a Table that illustrates that discodermolide is effective in inhibiting the growth of a number of different types of cancer cells.

In one aspect, this invention relates to the use of discodermolide to inhibit the growth of multidrug resistant cells. Multidrug resistance is a term known in the art that refers to cells which are resistant (i.e., the cells survive) to more than one antineoplastic agent. The term "antineoplastic agent" is used herein to refer to molecules that are able to inhibit growth of a cancer cell and are used in therapies to treat cancer in mammals. Cells can be multidrug resistant through a genetic mutation even though the cells have not been exposed to one or more antineoplastic agents. More commonly, multidrug resistance results from exposure to one antineoplastic agent which then selects for cells that are resistant to more than one other antineoplastic agent. Multidrug resistance is a major challenge in cancer chemotherapy because the resistance severely impairs the effectiveness of a number of clinically important drugs. Drugs that are known to induce multidrug resistance include, for example, Actinomycin D, anthracyclines such as daunorubicin, doxorubicin, etoposide, mitoxantrone, taxanes, such as paclitaxel, topoisomerase inhibitors such as etoposides, and Vinca alkaloids such as vinblastine and vincristine, vinorelbine and colchicine. Multidrug resistance occurs both in culture and in vivo. In general, cell lines that display the multidrug resistance phenotype are resistant to natural products, but retain their sensitivity to alkylating agents and antimetabolites.

A multidrug resistance gene family has been identified and appears to be part of the ABC (ATP-binding cassette) superfamily (reviewed by Bellamy in *Annu. Rev. Pharm. Toxicol.* 1996, 36:161–83). The more common member of this family is the protein, Pgp which is described vide supra. A second protein associated with multidrug resistance is MRP. MRP also confers resistance to numerous natural products. Like Pgp, MRP can be elevated in patients with acute and chronic leukemia and solid tumors.

The cells which are resistant to at least one antineoplastic agent are preferably contacted with discodermolide in vivo, preferably in a mammal. Although the cells can also be contacted with discodermolide in culture. A preferred mammal in this invention is a human; however, veterinary applications are additionally included within the scope of this invention.

Multidrug resistance can be monitored in culture or in vivo. Methods for monitoring and assessing multidrug resistance are well known and for that reason will not be described in detail here. In culture, cells which are able to grow or to survive in the presence of more than one antineoplastic agent as compared with matched, growth controlled cultures of cells including those obtained from normal, differentiated tissue are said to be multidrug resistant.

It is also possible to assess multidrug resistance in vivo and to assess multidrug resistance over time for or during a particular treament regime. For example, immunocytochemical assays are known in the art that assess levels of Pgp protein or other proteins belonging to the multidrug resistance family of proteins. In these assays it is possible to compare levels of the proteins in cancer cells as compared with normal, growth controlled cells. RNA assays or immunoblots have been described in the literature to monitor multidrug resistance as have in situ hybridization studies and flow cytometric assays.

To demonstate the growth inhibiting, and preferably cytotoxic effect of discodermolide for multidrug resistant cells in vivo, two different human tumor xenografts (HCT-15 and MIP 101) are separately implanted subcutaneously in athymic nude mice (see Example 2 below). NVP XAA296-NX results in statistically significant (p<0.01) and reproducible inhibition of tumor growth in both tumor models. The HCT-15 model is completely refractory to paclitaxel treatment, while the MIP 101 model is resistant to paclitaxel when administered at 15 mg/kg, once daily for the first five days.

Discodermolide administered as a single injection produces dose-dependent, statistically significant (p<0.01) inhibition of tumor growth for all tested doses in both xenograft models. Toxicity, as measured by body weight loss, appears to be tumor-dependent since an independent experiment demonstrates that naive (non-tumor bearing) athymic nude mice dosed with single injections of discodermolide lost no more than 4% of body weight one week after dosing and fullly recovered to the control levels in 3 weeks after dosing. These experiments demonstrate the antitumor efficacy of discodermolide in two tumor models that were resistant to paclitaxel. In both cases discodermolide was able to induce apoptosis. In further experiments it was demonstrated that discodermolide promoted phosphorylation of Raf-1, Bcl-2 and Bcl-$x_L$ In another aspect of this invention, the invention relates to methods for inhibiting the growth of cancer cells having mutation in a cellular protein that renders the cells resistant to at least one antineoplastic agent. An example of this mechanism of resistance are cells having a β-tubulin mutation that renders the cells resistant to taxanes, such as paclitaxel. In this aspect of the invention, the invention involves contacting at least one cell with a growth-inhibiting amount of discodermolide. Again, methods for determining whether or not cancer cells are growth inhibited are well known in the art. These studies include cell quantitation using cell counting techniques monitored over time, flow cytometry, and the like. In vivo, cell growth inhibition can be monitored in blood borne tumors by assessing tumor load over time. Similarly, the size of the tumor in situ can be monitored as can the progression or lack thereof of metastases. All of these methods are well known to those of ordinary skill in the art of oncology drug testing.

Recently published results of clinical studies suggest that mutations in β-tubulin are associated with resistance of solid tumors to paclitaxel (Monzo M, et al. *J. Clin. Oncol.* 1999, 17,(6):1786–1793). More than one mutation in the β-tubulin proteins have been described. These include a mutation in Alanine$^{364}$ and in several leucines within the β-tubulin amino acid sequence. This invention demonstrates that cells that are refractory to paclitaxel and have a β-tubulin mutation are sensitive to discodermolide therapy. Example 3 details experiments assessing discodermolide sensitivity using a paclitaxel-resistant ovarian carcinoma cell line, 1A9PTX22 and its parental cell line, 1A9, which is sensitive to paclitaxel. In these studies cells remain sensitive to discodermolide irrespective of the presence of a β-tubulin mutation.

There are several mutations in at least one β-tubulin protein that have been described as conferring resistance to cancer cells for at least one antineoplastic agent. The amino acid sequences for the two isotypes of native human β-tubulin are provided below as SEQ ID NO:1 and SEQ ID NO:2:

TABLE I

Amino Acid sequence of β-tubulin* (SEQ ID NO:1)

```
  1 mreivhiqag qcgnqigakf wevisdehgi dptgtyhgds dlqldrisvy
    yneatggkyv
 61 prailvdlep gtmdsvrsgp fgqifrpdnf vfgqsgagnn wakghytega
    elvdsvldvv
121 rkeaescdcl qgfqlthslg ggtgsgmgtl liskireeyp drimntfsvv pspkvsdtvv
181 epynatlsvh qlventdety cidnealydi cfrtlrlttp tygdlnhlvs gtmecvttcl
241 rfpgqlnadl rklavnmvpf prlhffmpgf apltsrgsqq yraltvpdlt
    qqvfdaknmm
301 aacdprhgry ltvaavfrgr msmkevdeqm lnvqnknssy fvewipnnvk
    tavcdipprg
361 lkmavtfign staiqelfkr iseqftamfr rkaflhwytg egmdemefte
    aesnmndlvs
421 eyqqyqdata eeeedfgeea eeea
```

Amino Acid sequence of β-tubulin* (SEQ ID NO:2)*

```
  1 mreivhlqag qcgnqigakf wevisdehgi dptgtyhgds dlqlerinvy
    yneatggnyv
 61 pravlvdlep gtmdsvrsgp fgqifrpdnf vfgqsgagnn wakghytega
    elvdavldvv
121 rkeaescdcl qgfqlthslg ggtgsgmgtl liskmreefp drimntfsvv pspkvsdtvv
181 epynatlsvh qlventdety cidnealydi cfrtlklttp tygdlnhlvs atmsgvttcl
241 rfpgqlnadl rklavnmvpf prlhffmpaf apltsrgsqq yrgltvpelt
    qqmfdaknmm
301 aacdprhgry ltvaavfrgr msmkevdeqm lsvqsknssy fvewipnnvk
    tavcdipprg
361 lkmavtfign staiqelfkr iseqftamfr rkaflhwytg egmdemefte
    aesnmndlvs
421 eyqqyqdata eqgefeeeae eeva
```

*swissprot: locus TBB5_HUMAN, accession P04350

In yet another aspect of this invention, the invention relates to the use of Discodermolide to treat cells resistant to platinating agents such as cisplatin and its analogues. In experients using methods identical to those described in Example 1, below, the ovarian cell lines 2008 and C13 are tested for sensitivity to discodermolide and to paclitaxel. C13 is resistant to paclitaxel and demonstrates an overproduction of glutathione. In experiments comparing paclitaxel and discodermolide, 2008 cells have $IC_{50}$s of 0.06 and 0.8 for discodermolide and paclitaxel respectively while the cisplatin resistant cells C13 have $IC_{50}$s of 0.03 and 12. These results demonste the utility of discodermolide as a treatment for cancer cells resistant to cisplatin or that overproduce glutathione.

The term "contacting" is used in this invention to refer to any suitable delivery method for bringing discodermolide in contact with the cancer cells that are resistant to at least one antineoplastic agent. For culture applications, merely adding solutions of discodermolide in a pharmaceutically acceptable buffer of cell culture medium is sufficent. For in vivo applications, discodermolide can be delivered to the cancer cells resistant to at least one antineoplastic agent using any suitable method known to those of ordinary skill in the art of drug delivery. Intravenous delivery and peritoneal delivery is preferred and those skilled in the art of drug delivery are familiar with the apparati designed for drug delivery via this route of administration.

Similarly, the pharmaceutically acceptable formulations comprising pharmacologically active discodermolide alone, or in combination with one or more pharmaceutically acceptable carriers, preferably suitable for parenteral application will be readily discernible to those of ordinary skill in the art. Such formulations may include suitable excipients. Preferred delivery formulations are provided in the examples below. These formulations include combinations of discodermolide with cremaphor, propylene glycol, propylene glycol with D5W, ethanol D5W or with saline.

In culture, effective doses used are typically those at the $IC_{50}$ concentration (see FIG. 1). In vivo acute toxic doses are determined in clinical trial by treating at fractions of the $IC_{50}$ and assess toxicity. Effective doses of discodermolide for the mouse are about (+/−5 mg/kg) 15 mg/kg given as one treatment every three weeks; for the rat; about (+/−0.5) 3 mg/kg administered as one treatment every three weeks; and for marmoset; about (+/−0.5) 1 mg/kg given as one treatment every three weeks. Preferred dosages and dosing regimes for man will of course be perfected following clinical trials using methods well known to those of ordinary skill in the art of clinical trials and will be optimized for particular types of cancer, however expected dosages are preferably from about 10 mg/kg to about 300 mg/kg in humans and more preferably from about 50 mg/kg to about 150 mg/kg of discodermolide.

While particular embodiments of the invention will be described in detail, it will be apparent to those of ordinary skill in the art that these embodiments are exemplary rather than limiting.

EXAMPLE 1

In vitro Growth Inhibition of Multidrug Resistant Cells

Preparation of Compound Solutions

A stock solution of discodermolide (natural product) at 10 mg/ml in 95% v/v ethanol is prepared and stored at −20° C. Aliquots are diluted directly either in cell culture media (for in vitro assays) or in phosphate buffered saline (PBS; for all in vivo experiments).

Cells and Cell Culture Conditions

The following cell lines are obtained from the American Type Culture Collection (ATCC, Rockville, Md., USA): human colon carcinomas HCT-15 (CCL 225) and HCT-116 (CCL 247), human lung adenocarcinoma A549 (CCL 185), human large cell carcinoma NCI-H460 (HTB 177), estrogen-independent breast carcinoma MDA-MB-231 (HTB 177), prostate cancer cell line Du 145 (HTB 81). The human KB-31 (drug-sensitive) and KB-8511 (multidrug-resistant, Pgp170 overexpressing) epidermoid carcinoma cells are obtained from Dr. R. M. Baker, Roswell Park Memorial Institute (Buffalo, N.Y., USA) and have been previously described (Akiyam S, et al. *Somatic Cell Molec Genetics* 1985;11:117–126 and Fojo A, et al., *Cancer Res.* 1997;45:3002–3007). The human metastatic prostate carcinoma PC-3M is obtained from Dr. I. J. Fidler (MD Anderson Cancer Center, Houston, Tex., USA). The estrogen-dependent human breast carcinoma cell line MCF-7/ADR (multidrug resistant) is a subline of the MCF-7 cell line (ATCC HTB 22) and is obtained from Dr. D. Fabbro (Novartis Pharma AG, Basel, Switzerland) and has been previously described (Blobe G C, et al. *J. Biol. Chem.* 1993; 268:658–664).

Antiproliferative Assay

For the antiproliferative assays, cells are seeded at 1.5× 103/well into 96-well microtiter plates and incubated overnight. Compounds are added in serial dilutions on day 1. The plates are than incubated for additional 5 days. This allowed the control cultures to undergo at least 3 cell divisions. After incubation the cells are fixed with 3.3% v/v glutaraldehyde, washed with water and stained with 0.05% w/v methylene blue. After washing, the dye is eluted with 3% v/v HCl and the optical density measured at 665 nm with a SpectraMax 340 (Bucherer, Basel, Switzerland). $IC_{50}$ values are determined by a computerized system (SoftPro, Bucherer, Basel, Switzerland) using the formula (OD test—OD start)/(OD control—OD start)×100. $IC_{50}$ is defined as the drug concentration which leads to 50% of cells per well compared to control cultures (100%) at the end of the incubation period.

Material

Natural discodermolide (sample 1) is obtained from Harbor Branch Oceanographic Institution (Ft. Pierce, Fla., USA). Synthetic discodermolide is prepared using any number of methods described in the art including, for example, the methods of Smith A B, PCT Publication Number WO 00/04865, the contents of which is incorporated by reference herein. Paclitaxel is obtained from Calbiochem (La Jolla, Calif., USA). Cell culture materials are from Integra BioSciences (Wallisellen, Switzerland). For HPLC, solvents are HPLC Gradient grade from Merck (Darmstadt, Germany). Liquid media, fetal bovine serum (FBS) and media additives are from Gibco/BRL (Basel, Switzerland).

Results

Antiproliferative Activity

The antiproliferative profile of discodermolide is determined against a panel of human tumor lines. As shown in Table 1, the compound showed potent antiproliferative activity in vitro with the $IC_{50}$ values in the low nanomolar range (~2–24 nM) for drug-susceptible cell lines. Paclitaxel, is a potent cytotoxic agent but is much less active than discodermolide against HCT-15 colon cells (~120 vs. ~8 nM $IC_{50}$ respectively). In the Pgp170-overexpressing, multidrug resistant KB-8511 and MCF-7/ADR lines, the loss of activity of paclitaxel was several fold higher than that shown by discodermolide.

Discussion

Discodermolide is more potent than paclitaxel against MCF-7/ADR cells, which is multidrug resistant due to overexpression of Pgp170, protein kinase-C, and glutathione S-transferase.

EXAMPLE 2

In vivo Growth Inhibition of Multidrug Resistant Cells

Cell Lines and Tissue Culture

All cell lines that are used in animal studies are free of Mycoplasma contamination (Rapid Detection System by Gen-Probe, Inc., San Diego, Calif.) and viral contamination (MAP testing by MA BioServices, Inc., Rockville, Md.). The HCT-15 human colon tumor cell line is purchased from the American Type Culture Collection, Rockville, Md., Accession Number ATCC CCL 225. The MIP 101 human colon tumor cell line is obtained from Dr. R. Kramer (Bristol Meyers Squibb) and was previously described (Niles R M, et al. *Cancer Invest.* 1987;5(6):545–52). These cells are Pgp-1 (human Pgp) overexpressors, making the cells resistant to paclitaxel. All cell lines are propagated and expanded in RPMI 1640 medium containing 10% heat-inactivated FBS (Life Technologies, Grand Island, N.Y.). Cell expansions for implantation are performed in T225 tissue culture flasks. Cells are harvested at 70–90% confluency, washed once with HBSS containing 10% FBS, and are suspended in plain HBSS.

Animals and Tumor Implantations

Outbred athymic (nu/nu) female mice ("Hsd:Athymic Nude-nu" from Harlan Sprague Dawley, Indianapolis, Ind.) are anesthetized with Metofane (Mallinckrodt Veterinary, Inc., Mundelein, Ill.,). A cell suspension (100 μL) containing $1 \times 10^6$ cells is then injected sc into the right axillary (lateral) region of each animal. Tumors are allowed to grow until a volume of approximately 100 $mm^3$ was achieved. At this point, mice bearing tumors are sorted into groups of eight for the study. The sorting process produced groups balanced with respect to mean and range of tumor size.

Drugs and Formulations

Discodermolide is isolated from the sponge *Discodermia dissoluta* using the methods of (Gunasekera S P, et al. supra). Multiple batches of compound of similar purity (all>95% pure, as determined by mass spectrometry, and nuclear magnetic resonance analysis) are used throughout the various studies. Solid discodermolide is dissolved in pure ethanol to create a stock solution which is diluted just before dosing with Cremophor EL (Crm) and D5W to a final concentration of 16.7% Cremophor EL, 8.3% ethanol and 75% D5W. The compound is administered intravenously (iv). In the first study discodermolide is tested against both tumors at five different dosing schedules: (i.) 30 mg/kg dosed as two 15 mg/kg injections on day 1 of the experiment, (ii.) 30 mg/kg dosed as three 10 mg/kg injections on days 1, 2, and 3, (iii.) 15 mg/kg dosed as a single injection on day 1, (iv.) 20 mg/kg dosed as a 15 mg/kg injection on day 1, followed by a 5 mg/kg injection on day 11, and (v.) 10 mg/kg dosed as a 7.5 mg/kg injection on day 1 followed by a 2.5 mg/kg injection on day 11. In the second study discodermolide is dosed as one injection on the first day of the experiment, at 2.5 mg/kg, 5 mg/kg, 7.5 mg/kg, 10 mg/kg, 12.5 mg/kg, or 15 mg/kg. In addition the 7.5 mg/kg injection on day 1 followed by a 2.5 mg/kg injection on day 11 is repeated from the first study. The actual doses, regimens and routes of administration used for the specific models are discussed in each section separately. Positive control animals receive clinical formulations of paclitaxel (TAXOL) diluted 4-fold with D5W and administered iv once daily for five consecutive days. Vehicle control for paclitaxel is administered according to paclitaxel's schedule. In the first study vehicle controls for discodermolide (16.7% Cremophor EL, 8.3% ethanol and 75% D5W) are administered as three daily injections on days 1, 2, and 3, or as two injections on days 1, and 11. In the second study vehicle control for discodermolide is administered as a single injection on day 1.

Tumors are measured, and individual animal body weights are recorded once weekly. Standard experiments are conducted for 3 full weeks from the initial dosing.

To assess toxicity of discodernolide on non-tumor bearing animals, four groups of 8 naive nude mice are dosed with the compound, iv, once (5 mg/kg, 7.5 mg/kg, 10 mg/kg, or 15 mg/kg). The control group is dosed with the vehicle alone (16.7% Cremophor EL, 8.3% ethanol and 75% D5W). Body weights are recorded once weekly.

Calculations of Results

Antitumor activity is expressed as % T/C (comparing Δ tumor volumes for treatment group to vehicle control group). Regressions are calculated using the formula: $(1-T/T_0) \times 100\%$, where T is the tumor volume for the treatment group at the end of the experiment, and $T_0$ is the tumor volume at the beginning of the experiment.

Statistical significance of the results is uniformly evaluated using a one-tailed Student's t-test following analysis of our representative experiments.

Results

A. Subcutaneous HCT-15 Colon Tumor Model

Results are determined for the first experiment in the HCT-15 colon tumors with discodermolide administered at: (i.) 30 mg/kg dosed as two 15 mg/kg injections on day 1 of the experment, (ii.) 30 mg/kg dosed as three 10 mg/kg injections on days 1, 2, and 3, (iii.) 15 mg/kg dosed as a single injection on day 1, (iv.) 20 mg/kg dosed as a 15 mg/kg injection on day 1, followed by a 5 mg/kg injection on day 11, and (v.) 10 mg/kg dosed as a 7.5 mg/kg injection on day 1 followed by a 2.5 mg/kg injection on day 11. All animals dosed with 30 mg/kg of discodermolide administered as three 10 mg/kg injections on days 1, 2, and 3, are sacrificed in the beginning of the third week of the experiment due to excessive body weight loss. Four animals from the group dosed 20 mg/kg administered as a 15 mg/kg injection on day 1, followed by a 5 mg/kg injection on day 11, die in the second week of the experiment. The remaining four animals from this group are sacrificed due to the excessive body weight loss. Discodermolide administered as a single 15 mg/kg injection on day 1 produces 43% T/C with 18.9% body weight loss. Two 15 mg/kg injections on day 1 (30 mg/kg total dose) results in 22% T/C, and 24.6% body weight loss. Administration of the compound at 10 mg/kg, as a 7.5 mg/kg injection on day 1 followed by a 2.5 mg/kg injection on day 11, gives 31% T/C associated with 17.3% body weight loss. All antitumor efficacy results are statistically significant (p<0.01). Paclitaxel, administered at 15 mg/kg, daily, for the first 5 days, is inactive in this experiment (95% T/C). In the second study discodermolide is dosed as one injection on the first day of the experiment, at 2.5 mg/kg, 5 mg/kg, 7.5 mg/kg, 10 mg/kg, 12.5 mg/kg, or 15 mg/kg. In addition the 7.5 mg/kg injection on day 1 followed by a 2.5 mg/kg injection on day 11 is repeated from the first study. Discodermolide dosed at 10 mg/kg, administered as a 7.5 mg/kg injection on day 1 followed by a 2.5 mg/kg injection on day 11, gives 29% T/C with 11.4% body weight loss. Single injections of 2.5 mg/kg, 5 mg/kg, 7.5 mg/kg, 10 mg/kg, 12.5 mg/kg, or 15 mg/kg discodermolide on day 1 of the experiment produces 62% T/C, 44% T/C, 43% T/C, 40% T/C, 28% T/C, and 27% T/C, respectively. Corresponding body weight changes are 3.5% (gain), −1.9%, −7.9%, −8.5%, −12.9%, and −11.0%. All antitumor efficacy results are statistically significant (p<0.01). In the second study paclitaxel is inactive (94% T/C). Repeat of the dose response in the third study, produces results similar to those obtained in the second experiment. Single injections of 2.5 mg/kg, 5 mg/kg, 7.5 mg/kg, 10 mg/kg, 12.5 mg/kg, or 15 mg/kg discodermolide on day 1 of the experiment produces 54% T/C, 43% T/C, 23% T/C, 27% T/C, 25% T/C, and 19% T/C, respectively. Corresponding body weight changes are 1.7% (gain), −8.9%, −23.3%, −17.6%, −20.1%, and −13.4%. All antitumor efficacy results are statistically significant (p<0.01). In the third study paclitaxel is inactive (81% T/C). Results for the HCT15 xenograft model and corresponding mean body weights are provided in FIG. 2.

B. Subcutaneous MIP 101 Colon Tumor Model

Figure 3:
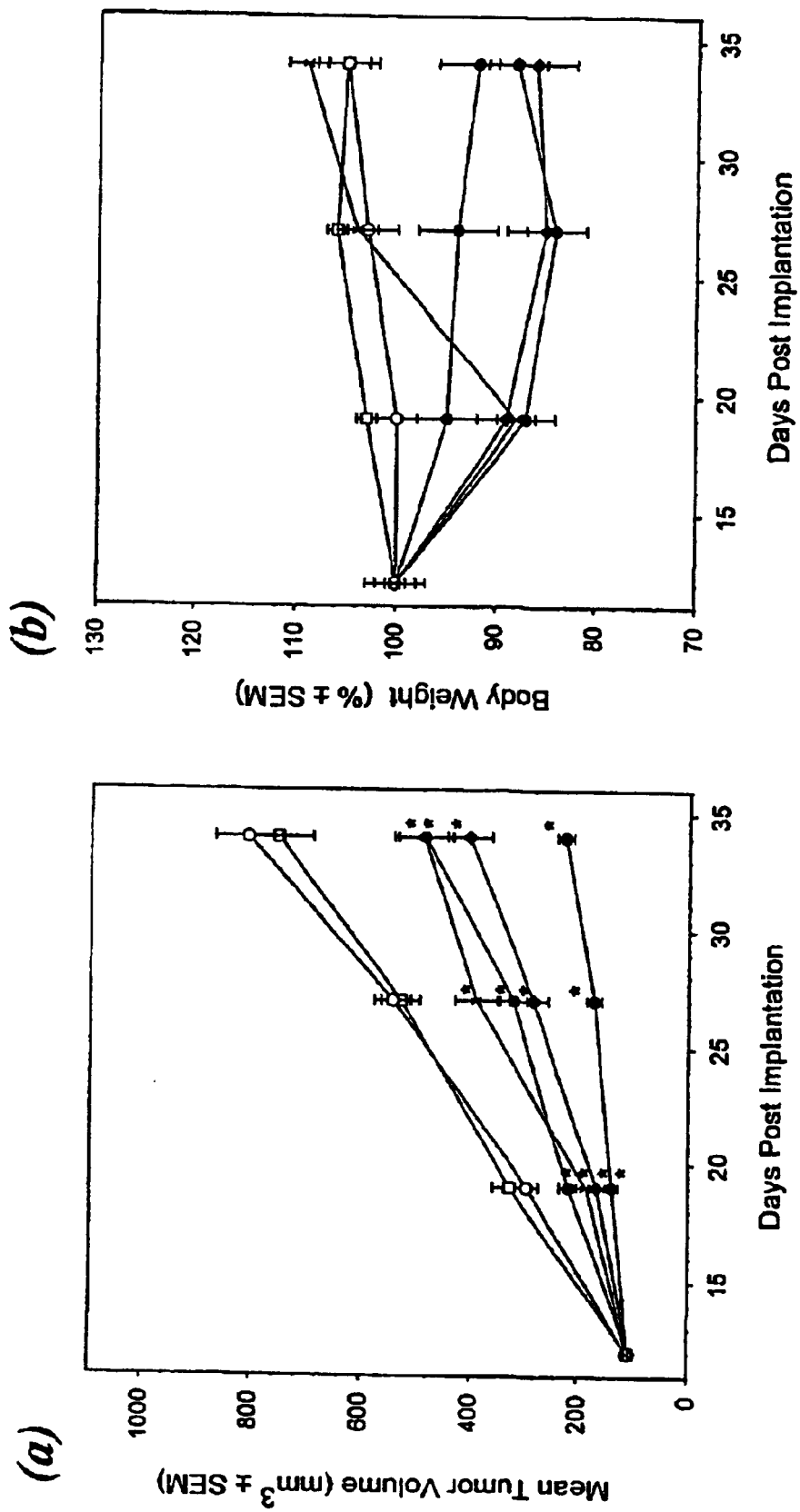
FIG. 3(a) provides the mean tumor volumes and FIG. 3(b) provides mean body weights in a study to assess paclitaxel-resistant (Pgp-1)-overexpressing humnn colon tumor xenograft (MIP 101 cells) sensitivity to discodermolide. —□— refers to control solution of 16.7% Crm.-8.3% EtOH/D5W, iv 1× (d.14); —●— refers to mice receiving discodermolide, iv, 15 mg/kg, 1× (d.14); —◆— refers to mice receiving discodermolide, iv, 7.5 mg/kg, 1× (d. 14); —◆— refers to mice receiving discodermolide, iv, 2.5 mg/kg, 1× (d 14); —○— refers to mice receiving 12.5% Crm-12.5% EtOH/D5W, iv, 1×/day (d. 14–16); and —x— refers to mice receiving paclitaxel, iv, 15 mg/kg, 1×/day (d. 14–18).

Results for the first experiment in the MIP 101 colon tumors with discodermolide is determined for data points gathered from mice administered: (i.) 30 mg/kg dosed as two 15 mg/kg injections on day 1 of the experiment, (ii) 30 mg/kg dosed as three 10 mg/kg injections on days 1, 2, and 3, (iii.) 15 mg/kg dosed as a single injection on day 1, (iv.) 20 mg/kg dosed as a 15 mg/kg injection on day 1, followed by a 5 mg/kg injection on day 11, and (v.) 10 mg/kg dosed as a 7.5 mg/kg injection on day 1 followed by a 2.5 mg/kg injection on day 11. All animals dosed with 30 mg/kg of discodermolide administered as three 10 mg/kg injections on days 1, 2, and 3, die on day 5 of the experiment. All animals from the group dosed with 20 mg/kg administered as a 15 mg/kg injection on day 1, followed by a 5 mg/kg injection on day 11 are sacrificed in the beginning of the third week of the experiment due to the excessive body weight loss. Discodermolide is administered as a single 15 mg/kg injection on day 1 produced 36% T/C (treated vs. control) with 18.9% body weight loss. Two 15 mg/kg injections on day 1 (30 mg/kg total dose) result in 24% T/C, and 23.4% body weight loss. Administration of the compound at 10 mg/kg, as a 7.5 mg/kg injection on day 1 followed by a 2.5 mg/kg injection on day 11, gives 38% T/C associated with 21.3% body weight loss. All antitumor efficacy results are statistically significant (p<0.01). Paclitaxel, administered at 15 mg/kg, daily, for the first 5 days, is inactive in this experiment (82% T/C). In the second study discodermolide is dosed as one injection on the first day of the experiment, at 2.5 mg/kg, 5 mg/kg, 7.5 mg/kg, 10 mg/kg, 12.5 mg/kg, or 15 mg/kg. In addition the 7.5 mg/kg injection on day 1 followed by a 2.5 mg/kg injection on day 11 is repeated from the first study. Results are presented graphically in FIG. 2. Discodermolide dosed at 10 mg/kg, administered as a 7.5 mg/kg injection on day 1 followed by a 2.5 mg/kg injection on day 11, gives 35% T/C with 11.4% body weight loss. One animal in that group dies from apparent drug toxicity. Single injections of 2.5 mg/kg, 5 mg/kg, 7.5 mg/kg, 10 mg/kg, 12.5 mg/kg, or 15 mg/kg discodermolide on day 1 of the experiment produces 59% T/C, 57% T/C, 46% T/C, 37% T/C, 22% T/C, and 18% T/C, respectively. Corresponding body weight losses are 7.9%, 10.2%, 13.2%, 18.7%, 15.5%, and 11.7%. All antitumor efficacy results are statistically significant (p<0.01). In the second study paclitaxel showed statistically significant inhibition of tumor growth (54% T/C, p<0.01). Results are summarized in FIG. 3.

C. Toxicity of Discodermolide in non-tumor Bearing Animals

Naive animals are dosed with 5, 7.5, 10, or 15 mg/kg of discodermolide administered as a single injection of the experiment. One week after dosing animals demonstrate the following body weight changes: +8.7%, +1.2%, −1.2%, and −4.1%, respectively. Two weeks after dosing corresponding body weight changes are +9.4%, +3.2%, +1.2%, and −0.4%. Three weeks after dosing all animals gained weight as follows: +9.4%, +7.7%, +5.6%, and +5.90%. Animals dosed with the vehicle alone demonstrate the following body weight changes in each week of the experiment: +5.5%, +4.7%, and +5.9%. After a single iv administration the compound caused only minimal, and transient, body weight loss in these animals, and only at 10 mg/kg, and 15 mg/kg doses.

D. Discussion

In both colon models, HCT-15, and MIP 101, discodermolide, administered as single injection, demonstrated a dose-dependent, statistically significant inhibition of tumor growth at all doses between 2.5 mg/kg and 15 mg/kg. The HCT-15 model is totally refractory to treatment with paclitaxel, while the MIP 101 model shows no response in the first study (82% T/C), although in the second study paclitaxel produces a modest, but statistically significant inhibition of tumor growth (54% T/C, P<0.01).

For both tumor models only two dosing schedules from the first study are repeated in the second experiment; the repeated schedules demonstrate good reproducibility between the two experiments. In the HCT-15 model a single 15 mg/kg injection of discodermolide produces 43% T/C in the first study, and 27% T/C in the second study. A total dose of 10 mg/kg administered as two injections, a 7.5 mg/kg on day 1 followed by a 2.5 mg/kg on day 11 resulted in 31% T/C in the first study, and 29% T/C in the retest. In the MIP 101 model a single 15 mg/kg injection of the compound gave 36% T/C in the first experiment, and 18% T/C in the retest. Discodermolide at a total dose of 10 mg/kg administered as two injections, a 7.5 mg/kg on day 1 followed by a 2.5 mg/kg on day 11 produces 38% T/C in the first study, and 35% T/C in the retest.

In the HCT-15 model the dose response study is repeated in the third expeiment. Antitumor efficacy of the discodermolide demonstrates good reproducibility for all doses between 2.5 mg/kg, and 15 mg/kg (62% T/C and 54% T/C for 2.5 mg/kg, 44% T/C and 43% T/C for 5 mg/kg, 43% T/C and 23% T/C for 7.5 mg/kg, 40% T/C and 27% T/C for 10 mg/kg, 28% T/C and 25% T/C for 12.5 mg/kg, 27% T/C and 19% T/C for 15 mg/kg). In the repeat of the dose response study body weight losses are higher, reaching 23%, compared to 13% in the original study.

In conclusion, discodermolide shows dose-dependent antitumor efficacy in two known multidrug resistant tumor lines grown as xenografts in nude mice.

EXAMPLE 3

In vitro and In vivo Antitumor Effect of Discodermolide to Paclitaxel Resistant Cells having β-Tubulin Mutation Cell Lines and Tissue Culture All cell lines are free of Mycoplasma contamination (Rapid Detection System by Gen-Probe, Inc., San Diego, Calif.). The LS174T human colon tumor cell line is purchased from the American Type Culture Collection, Rockville, Md. The 1A9 and the 1A9PTX22 ovarian tumor cell lines are obtained from Dr. T. Fojo, Medicine Branch, Division of Clinical Sciences, National Cancer Institute, National Institutes of Health, Bethesda, Md. 20892. The 1A9 is a clone of the ovarian carcinoma cell line, A2780 (Eva A, et al. *Nature* 1982, 295:116–119). The 1A9PTX22 subline is isolated as an individual clone from the 1A9 cell line in a single step selection by exposure to 5 ng/mL paclitaxel in the presence of 5 μg/mL verapamil. The 1A9PTX22 cell line is found to be 24-fold more resistant to paclitaxel than the parental 1A9 (Giannakakou P, et al., *J. Biol. Chem.* 1997, 272(4):17118–17125). Resistance to paclitaxel is maintained following 2 years of culturing in a drug-free media, and was attributed to the Ala$^{364}$→Thr mutation in β-tubulin that is found in the 1A9PTX22 cell line. All cell lines are propagated and expanded in RPMI 1640 medium containing 10% heat-inactivated FBS (Life Technologies, Grand Island, N.Y.) in a tissue culture incubator (37° C., controlled, humidified atmosphere containing 5% $CO_2$). Cell expansions are performed in T75 tissue culture flasks (COSTAR, Corning, N.Y.). For hollow fiber preparations, cells are harvested at 70–90% confluency using 0.25% Trypsin-EDTA (Life Technologies, Grand Island, N.Y.).

In vitro Cytotoxicity Assay

1A9 and 1A9PTX22 cells are plated in 96-well plates at $5 \times 10^4$ cells/well, plced in a tissue culture incubator and allowed to attach overnight. The next morning, the number of viable cells in the "time 0" plate (3 wells for each cell line) is determined using an MTT assay (Alley M C, et al., *Cancer Res.* 1988, 48:589–601).

At the same time drugs are added in serial, 10-fold dilutions, to the experimental plates. Corresponding vehicles are added to control plates. Experimental and control plates are then incubated in the tissue culture incubator for 72 hours. After the incubation the number of viable cells is determined in each plate using the MTT assay. $IC_{50}$s (defined as a concentration of a given compound causing 50% inhibition of cell growth) are determined by comparing cell growth in the drug-treated plate ($T-T_0$) to the cell growth in the corresponding control plate ($C-T_0$). For each experiment results are calculated using average numbers from two sets of plates.

Preparation of Hollow Fibers

PVDF hollow fibers (Spectrum, Gardena, Calif.) are soaked in 70% EtOH for 72 hours before use. After this step, all handling of fibers are done under a biological laminar flow hood using aseptic procedures. Individual fibers are flushed with 3 mL of the ice-cold tissue culture media using a syringe equipped with a 20-gauge needle. Next, each fiber is filled with an appropriate cell suspension ($1 \times 10^6$ cells/mL for the 1A9 and 1A9PTX22 cells, and $0.5 \times 10^6$ cells/mL for the LS 174T cells), and both ends of the fiber are sealed with a hot flat needle holder. The entire length of the fiber is then sealed into 1.5 cm microcapsules (further called "hollow fibers"), each containing approximately 15 uL of the appropriate cell suspension. After separation, individual hollow fibers are placed in 6 well plates (6 fibers in 5 mL media per well), and are incubated overnight at 37° C. in the tissue culture incubator.

Implantation of Hollow Fibers

Outbred athymic (nu/nu) female mice ("Chrls:Athymic Nude-nu", Charles River Laboratories, Wilmington, Mass.) are anesthetized with ip injections of Ketamine/Xylazine (150 mg/kg, and 12 mg/kg body weight, respectively). For the subcutaneous implantation an 11-gauge trocar containing one or two hollow fibers is inserted into an incision made with scissors at the nape of the neck of an animal, and fibers are released by retracting the trocar while depressing the plunger. This procedure is repeated until all three hollow fibers are implanted. One wound clip is used to close the skin incision After the surgery each animal receives a single, subcutaneous injection of 0.4 mg/kg butorphenol to relieve any potential pain. Animals recover from the anesthesia on a heating pad, before retuning to their cages.

In vivo Hollow Fiber Assay

One day after the implantation (3 hollow fibers/animal, each hollow fiber containing one cell line: LS 174T, 1A9, and 1A9PTX22) animals are randomly sorted into five groups of six mice/group. The first group is sacrificed; hollow fibers are retrieved, and processed according to a published procedure (Hollingshead M G, et al. *Life Sciences* 1995, 57(2):131–141), to determine the number of viable cells in each fiber ($T_0$.)

The remaining groups are treated as follows:
Group 1: Discodermolide, 15 mg/kg, iv, once.
Group 2: Vehicle for discodermolide (16.7% Crem. EL, 8.3% Ethanol, 75% D5W), iv, once.
Group 3: Paclitaxel, 15 mg/kg, iv, daily for 5 days.
Group 4: Vehicle for paclitaxel (12.5% Cremophor EL, 12.5% Ethanol, 75% D5W), iv, daily for 5 days.

On day 6 all animals are sacrificed, and hollow fibers are retrieved, and processed according to Hollingshead, M G, (supra) to determine the number of viable cells in each fiber (T—for fibers from animals treated with experimental compounds, C—for fibers from animals treated with corresponding vehicles). Antitumor activity is expressed as % Mean ΔT/Mean ΔC [comparing cell growth for treatment group to vehicle control group, where % Mean ΔT/Mean ΔC=(Mean T—Mean $T_0$/Mean C—Mean $T_0$)×100%]. Regressions are calculated using the formula: (1–Mean T/Mean $T_0$)×100%. Statistical significance of the results is uniformly evaluated using a two-tailed Student's t-test.

Experimental Compounds and Formulations

Discodermolide is isolated from the sponge *Discodermia dissoluta* using the method of Gunasekera SP (supra). Multiple batches of compound of similar purity (all>95% pure, as determined by mass spectrometry, and nuclear magnetic resonance analysis) are used throughout the various studies. For the in vitro cytotoxicity assays all compounds are dissolved in DMSO and are added to the plates with cells to obtain desired concentrations. The amount of DMSO in cell cultures did not exceed 0.1% v/v. Paclitaxel is purchased from Sigma/Aldrich, (St. Louis, Mo.). For the in vivo hollow fiber assay, solid discodermolide is dissolved in pure ethanol to create a stock solution which is diluted just before dosing with Cremophor EL and D5W to a final concentration of 16.7% Cremophor EL, 8.3% ethanol and 75% D5W. The compound is administered to mice as a single, 15 mg/kg iv injection. Positive control animals receive clinical formulations of paclitaxel (TAXOL) diluted 4-fold with D5W (12.5% Cremophor El, 12.5% ethanol and 75% D5W final concentrations) and administered iv, at 15 mg/kg, once daily for five consecutive days. Vehicle controls are administered according to the corresponding drug schedules.

Results

In vitro Cytotoxicity

Figure 5:
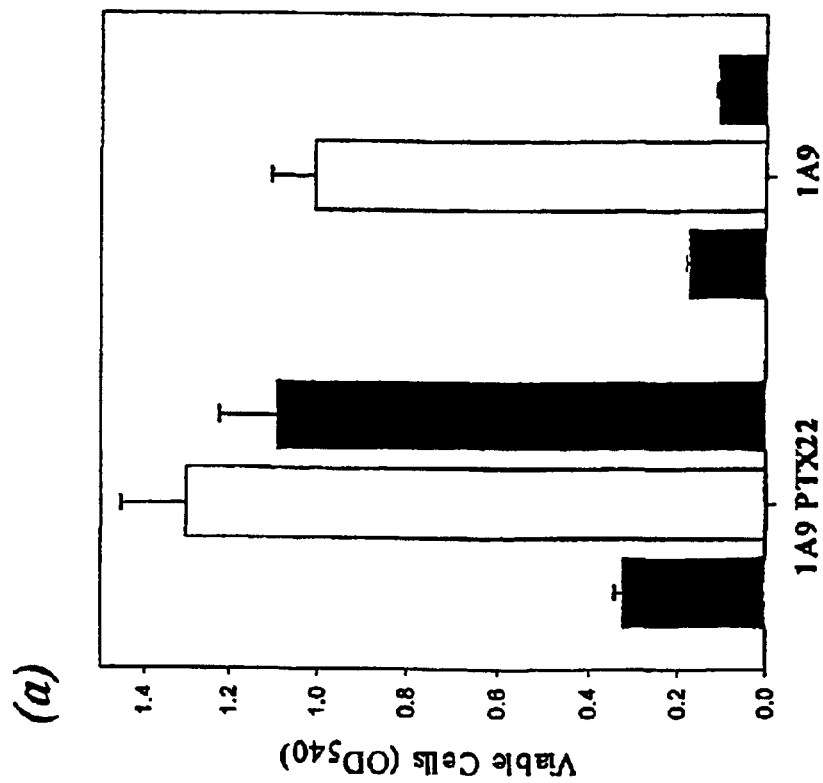
FIG. 5 illustrates results of experiments demonstrating that Paclitaxel-resistant 1A9PTX22 cells are sensitive to discodermolide in nude mice.

Results of the first experiment are summarized in FIG. 5, however, all experiments were performed in duplicate. In the 1A9 cell line the $IC_{50}$s for paclitaxel, and discodermolide are 0.8 ng/ml, and 6 ng/ml, respectively. In the paclitaxel-resistant 1A9PTX22 cell line, the corresponding $IC_{50}$s are: 15 ng/ml, and 3 ng/ml. In the 1A9 cell line $IC_{50}$s for, paclitaxel, and discodermolide are 0.4 ng/ml and 3 ng/ml, respectively. In the paclitaxel-resistant 1A9PTX22 cell line the corresponding $IC_{50}$s are 9 ng/ml, and 3 ng/ml.

In vivo Hollow Fiber Assay

Figure 4:
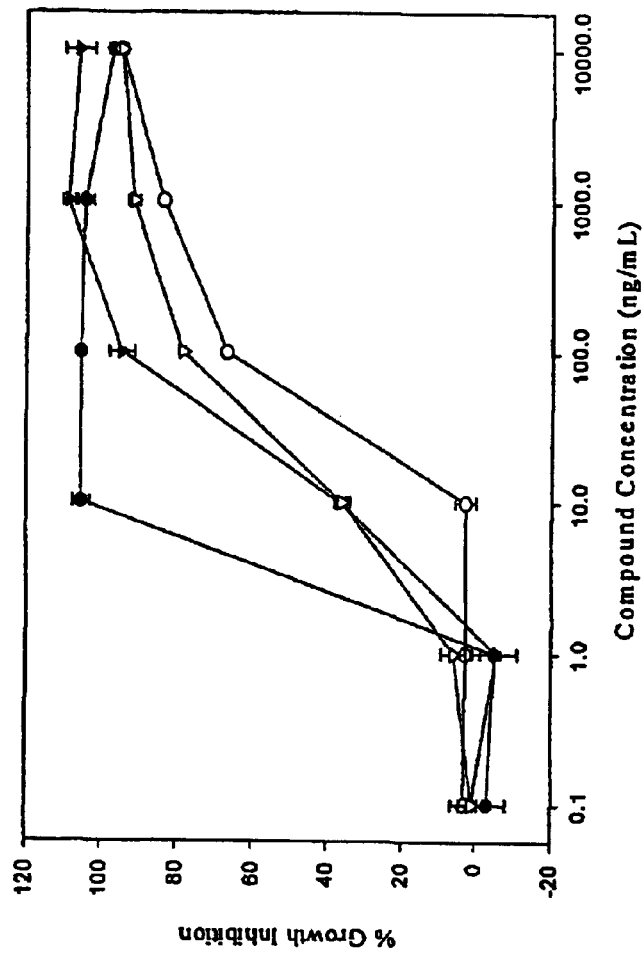
FIG. 4 assesses paclitaxel-resistant 1A9PTX22 (β-tubulin mutation) cell sensitivity to discodermolide. —●— refers to 1A9 cells receiving paclitaxel; —○— refers to 1A9PTX22 cells receiving paclitaxel; —▼— refers to 1A9 cells receiving discodermolide; and —▽— refers to 1A9PTX22 cells receiving discodermolide.

Results of the antitumor activity of paclitaxel and discodermolide against three human solid tumor cell lines subcutaneously implanted into nude mice in hollow fibers are summarized in FIG. 4. Paclitaxel, dosed iv, at 15 mg/kg, once daily, for 5 days produced T/C of 3%, −8%, and 79%, in LS 174T, 1A9, and 1A9PTX22 cell lines, respectively. Discodermolide, administered as a single, 15 mg/kg, iv injection, gave 7%, 8%, and −13% T/C in the respective cell lines. Paclitaxel, dosed iv, at 15 mg/kg, once daily, for 5 days produced T/C of 8%, 2%, and 90%, in LS 174T, 1A9, and 1A9PTX22 cell lines, respectively. Discodermolide is administered as a single, 15 mg/kg, iv injection, gave 13%, 14%, and 13% T/C in the respective cell lines. In both experiments animals dosed with paclitaxel lost 5% of their body weights, and animals dosed with discodermolide lost 10% of their body weights.

Discussion

The 1A9PTX22 cell line was derived from a 1A9 clone of an ovarian carcinoma cell line A2780 (Eva A, et al. *Nature* 1982, 295:116–119) by exposure to paclitaxel (Giannakakou P, et al. *J. Biol. Chem.* 1997, 272(4):17118–17125). The 1A9PTX22 cell line shows 24-fold resistance to paclitaxel in vitro, compared to the parental 1A9. This level of resistance is maintained after the cell line is cultured for 2 years in the absence of paclitaxel. It was shown that the 1A9PTX22 cell line contains an $Ala^{364} \rightarrow Thr$ mutation in β-tubulin, and that paclitaxel does not induce polymerization of the mutated tubulin prepared from the 1A9PTX22 cells (Giannakakou P., supra). Taken together these data suggest that mutations in β-tubulin are likely responsible for the resistance to paclitaxel.

Here we examine in vitro, and in vivo sensitivity of the 1A9 and 1A9PTX22 cell lines to discodermolide, a natural product, that, like paclitaxel, exerts its cytotoxicity by stabilizing tubulin polymers. In two, separate in vitro cell growth inhibition experiments, both, 1A9 and 1A9PTX22 cell lines showed similar sensitivity to discodermolide (for 1A9 $IC_{50}$s were 6 ng/mL, and 3 ng/mL, and for 1A9PTX22 $IC_{50}$s were 3 ng/mL for both experiments). In contrast, the 1A9PTX22 cell line is 20-fold more resistant to paclitaxel then the parental 1A9 cells (for 1A9 cells $IC_{50}$s were 0.8 ng/mL, and 0.4 ng/mL, and for 1A9PTX22 cells $IC_{50}$s are 15 ng/mL, and 9 ng/mL). Doxorubicin, used as a mechanistically unrelated cytotoxic control, produced the $IC_{50}$s of 3 ng/mL for 1A9 cells, and 3–5 ng/ml for 1A9PTX22 cells, showing that the latter is only slightly (2 fold) less sensitive to this compound than the parental 1A9 cell line. In order to determine how the in vitro sensitivity of the paclitaxel-resistant 1A9PTX22 cell line to discodermolide translates into the in vivo response, the compound is tested in the hollow fiber assay. A third cell line, colon carcinoma LS 174T is used in this experiment as an additional positive control. Both discodermolide and paclitaxel are dosed iv, at optimal concentrations and dosing schedules as described in Example 2. Discodermolide is administered once, at 15 mg/kg, and paclitaxel is administered once daily for 5 days at 15 mg/kg. The 1A9PTX22 cell line is sensitive to treatment with discodermolide (13% regression in the first study, and 13% T/C in the retest, both p<0.01), but is completely refractory to paclitaxel (79% T/C in the first study, and 90% T/C in the retest, both p>0.05). The LS 174T cell line is equally sensitive to both compounds. These results suggest that discodermolide can provide an effective therapy against tumors resistant to paclitaxel due to mutations in tubulin.

EXAMPLE 4

Discodermolide Induces Raf-1 Phosphorylation

Cell Culture Conditions

A549, a human non-small cell lung carcinoma and MDA-MB-435, a human breast carcinoma, used in this study are obtained from the American Type Culture Collection (ATCC, Rockville, Md., USA). MDA-MB-435 cells are maintained in MEM containing 10% FBS, 1% sodium pyruvate, 1% MEM non-essential amino acids, and 15 mM HEPES (pH=7.4). A549 cells are maintained in RPMI 1640 containing 10% FBS. 1A9, a single-cell clone of the human ovarian carcinoma cell line A2780 and PTX22, the paclitaxel-resistant subline, used in this stdy are obtained from M. Wartman (Novartis Pharmauticals). 1A9 cells and PTX22 cells are maintained in RPMI 1640 supplemented with 10% FBS. PTX22 maintenance media also contained 15 ng/mL paclitaxel and 5 μg/mL verapamil. Drug is removed from the media for 5–7 days before use in an experiment. All maintenance media contained 100 units/mL penicillin and 100 μg/mL streptomycin.

Antiproliferative Assays

Cell lines are trypsinized and counted using a Coulter counter. Cells were plated in 96 well plates (190 μL/well) at the following densities: 1,000 cells/well for A549 and 3,000 cells/well for MDA-MB-435. The number of cells plated results in cell densities of 75–90% confluence by the time of harvest. Plates are seeded on day 0. On day 1 test compounds are added to triplicate wells in a final volume of 10 μL media. Initial cell density for each cell line is measured on day 1 by adding 10 μL MTS mixture (see below), incubating for 4 h and recording absorbance at 490 nm (A490). Two or three days after test compound addition, 10 μL/well of MTS mixture is added to the test plates and $A_{490}$ was read 4 h later. $A_{490}$ values for wells containing cells are corrected for media absorbance, then normalized to initial density readings to determine percent net growth. Percent net growth is calculated as $(A_{490}+drug-A_{490}$ initial$)/(A_{490}$—drug—$A_{490}$ initial$)$. Graphs of percent net growth as a function of compound concentration are used to calculate concentrations resulting in 50% growth inhibition ($IC_{50}$). MTS mixture is prepared fresh on day of addition to cell plates at a ratio of 10 μL of a 0.92 mg/mL solution of phenazine methosulfate (PMS) to 190 μL of a 2 mg/mL solution of MTS (3-(4,5-dimethylthiazol-2-yl)-5-(3-carboxymethoxyphenyl)-2-(4-sulfophenyl)-2H-tetrazolium, inner salt). PMS and MTS solutions are prepared in buffered saline containing 0.2 g/L KCl, 8.0 g/L NaCl, 0.2 g/L $KH_2PO4$, 1.15 g/L $Na_2HPO_4$, 133 mg/L $CaCl_2.2H_2O$, 100 mg/L $MgCl_2.6H_2O$, (pH=7.35) and stored as foil-wrapped aliquots at −20° C. Test compounds are prepared as stock solutions in DMSO. Test compound dilutions are made in 2% DMSO/cell maintenance media and diluted into assay plates to give 0.1% DMSO final in all wells.

Western Blots

Cells are plated at a density of $1.5\times10^6$ cells per 100 mm plate. The next day cells are treated with vehicle control (0.1% DMSO) or test compound for 24 h. Cells are harvested by washing monolayers twice with PBS, then lysing with 300 ul of lysis buffer[20 mM Tris (pH 8.0), 2 nM EDTA, 100 mM NaCl, 0.5% NP40, 0.0125% DOC, 2.5% glycerol, 1 mM vanadate, 25 mM sodium fluoride and protease inhibitor cocktail (1:500 dilution, Sigma)]. Lysates were spun at 12,000× g and the supernatant transferred to a new tube. Protein concentration of the lysates is determined using BCA protein assay Reagent (Pierce). Samples (75 μg) are resolved by SDS-PAGE on a 7.5% or 14% tris-glycine gel for Raf-1 and Bcl-$x_L$, respectively, and transferred to nitrocellulose. Immunodetection is performed as described by Amersham Vistra Fluorescence Western blotting Kit directions with the following modifications: the membrane is blocked with 5% milk (Carnation Non-Fat Dry Milk) in buffer containing 20 mM Tris-HCl (pH=7.4), 100 mM NaCl, and 0.2% Tween 20 (TBST) overnight and is subsequently incubated for 2 h with primary antibody (Santa Cruz C-12 for Raf-1 and Santa Cruz H-62 for Bcl-$x_L$), followed by fluorescein-linked anti-rabbit Ig in 5% milk and anti-fluorescein alkaline phosphatase conjugate in TBST at 1:500 and 1:2000 dilutions, respectively. A Storm 860 (Molecular Dynamics) is used to detect fluorescent product according to the manufacturer's instructions.

Results

The effects on cell proliferation following a 72 h exposure to discodermolide was measured by MTS assays. The $IC_{50}$ values are determined in two independent experiments to be 45 and 60 nM for A549 cells, 3 and 15 nM for MDA-MB-435 cells, 10 and 39 nM for 1A9 cells and 23 and 37 nM for PTX-22 cells. Cells are treated with 50, 100 and 180 nM discodermolide and MDA-MB-435 cells are treated with 2, 20, 50 and 90 nM discodermolide to determine the effects of discodermolide treatment on Raf-1 and Bcl-$x_L$ phosphorylation. The paclitaxel concentration used as a positive control in the study was the same as used in Example 2.

Both Raf-1 and Bcl-$x_L$ are phosphorylated following 24 hour treatment of A549 and MDA-MB-435 cells with paclitaxel or discodermolide. Phosphorylation of Raf-1 is observed by the appearance of additional bands migrating more slowly and phosphorylation of Bcl-$x_L$, is observed by the broadening of a single band. Raf-1 phosphorylation is concentration-dependent, since in A549 and MDA-MB-435 cells the doublet is only observed at the higher concentrations tested. These results are consistent with previous studies in which the effects of paclitaxel on Raf-1 phosphorylation are also shown to be concentration dependent (Torres K and Horwitz S B. *Cancer Res.* 1998:58:3620–3626). Interestingly, Raf-1 phosphorylation is not required for cell death since low concentrations of paclitaxel led to apoptosis without Raf-1 phosphorylation perhaps through p21 and or p53 mediated apoptotic pathways. The minimmum paclitaxel concentration required for Raf-1 phosphorylation coincides with the induction of the G2/M block suggesting that Raf-1 activation may be a component of the signal cascade activated during the mitotic checkpoint. Since the discodermolide concentration required to induce Raf-1 phosphorylation was greater than the $IC_{50}$ value, it is likely that similar concentration specific discodermolide activities also exist. For example, treatment of A549 and MDA-MB435 cells at the $IC_{50}$ values is likely to induce cell death but not Raf-1 phosphorylation.

In order to determine whether discodermolide is potentially potent on tumor cells that are resistant to paclitaxel, we examined the effects of discodermolide on 1A9 ovarian carcinoma cells and a paclitaxel resistant subline, PTX-22. Paclitaxel resistance is not due to reduced paclitaxel accumulation but is associated with failure of tubulin polymerization in cells, cellular extracts or purified tubulin. This subline is reported to be 20–30-fold less sensitive to paclitaxel but does retain sensitivity to Vinca alkaloids. The paclitaxel 72 hour $IC_{50}$ value shifts from 6 nM on 1A9 cells to 80 nM on PNX-22 cells (13-fold less sensitive). Interestingly, discodermolide shows no cross-resistance as measured by $IC_{50}$, which are 25 and 30 nM on 1A9 and PTX-22 cells, respectively. Raf-1 is phosphorylated in 1A9 parental cells treated with both paclitaxel and discodermolide and in the PTX-22 cells treated with discodermolide., Raf-1 phosphorylation is not observed in the PTX-22 cells following paclitaxel treatment. These studies suggest that discodermolide may be useful in treating tumors that are paclitaxel-resistant.

What is claimed is:

1. A method for inhibiting the growth in vivo of multidrug resistant cells comprising the step of:
   contacting at least one multidrug resistant cell with a growth inhibiting amount of discodermolide wherein the multidrug resistant cell is selected from colon, lung, breast, ovarian, prostate and epidermoid cells.

2. The method of claim 1 wherein the multidrug resistant cell is resistant to taxanes.

3. The method of claim 1 wherein the multidrug resistant cell is resistant to paclitaxel.

4. The method of claim 1 wherein the cell is from a mammal.

5. The method of claim 4 wherein the mammal is a human.

6. A method for inhibiting the in vivo growth of a cancer cell comprising the steps of;
   contacting at least one cancer cell with a growth inhibiting amount of discodermolide wherein the cancer cell is resistant to at least one antineoplastic agent wherein the cancer cell is selected from colon, lung, breast, ovarian, prostate and epidermoid cells.

7. The method of claim 6 wherein the cancer cell is a multidrug resistant cell.

8. The method of claim 6 wherein the cell comprises a mutation in β-tubulin.

9. The method of claim 6 wherein the cell over produces glutathione.

10. The method of claim 6 wherein the cell is in a mammal.

11. A method for promoting apoptosis in a multidug resistant cell in vivo comprising the steps of:
    contacting a multidrug resistant cell with discodermolide; and inducing apoptosis in the cell wherein the mulidrug resistant cell is selected from colon, lung, breast, ovarian, prostate and epidermoid cells.

12. The method of claim 11 wherein the muitidrug resistant cell is resistant to paclitaxel.

13. The method of claim 11 wherein the cell is in a mammal.

14. The method of claim 13 wherein the mammal is a human.

15. A method for inhibiting the growth in vivo of cancer cells having a β-tubulin mutation comprising the steps of;
contacting at least one cancer cell with a growth inhibiting amount of discodermolide wherein the cell comprises a mutation in the protein β-tubulin; and
inhibiting cell division in the cell wherein the cancer cell is selected from colon, lung, breast, ovarian, prostate and epidermoid cells.

16. The method of claim 15 wherein the cell is resistant to paclitaxel.

17. The method of claim 15 wherein the cell is in a mammal.

18. The method of claim 17 wherein the mammal is a human.

19. A method for inhibiting in vivo growth of a tumor resistant to at least one antineoplastic agent comprising the step of:
contacting a tumor with discodermolide wherein the tumor comprises cells resistant to at least one antineoplastic agent wherein the tumor is selected from colon, lung, breast, ovarian, prostate and epidermoid cells.

20. The method of claim 19 wherein the cells have a mutation in a β-tubulin protein.

21. The method of claim 19 wherein the cells overproduce glutathione.

22. The method of claim 19 wherein the cells are mulidrug resistant.

23. The method of claim 19 wherein the cells comprise raf-1 and wherein raf-1 is phosphorylated in the presence of discodermolide.

24. The method of claim 19 wherein the at least one neoplastic agent is paclitaxel.

25. A method for inhibiting the growth of multidrug resistant cells comprising the step of contacting at least one multidrug resistant cell with a growth inhibiting amount of discodermolide, wherein the multidrug resistant cells are selected from the group consisting of a lung cells, prostate cells and epidermoid cells.

26. The method according to claim 25 wherein the cell growth is in vivo.

27. The method according to claim 25 wherein the cell growth is in vitro.

28. The method of claim 25 wherein the multidrug resistant cell is resistant to taxanes.

29. The method of claim 25 wherein the multidrug resistant cell is resistant to paclitaxel.

30. A method for inhibiting the growth of a cancer cell comprising the steps of contacting at least one cancer cell with a growth inhibiting amount of discodermolide wherein the cancer cell is selected from the group consisting of a lung cell, prostate cell, and an epidermoid cell and where in the cancer cell resistant to at least one antineoplastic agent.

31. The method according to claim 30 wherein the cell growth is in vitro.

32. The method according to claim 30 wherein the cell growth is in vivo.

33. The method of claim 30 wherein the cancer cell is a multidrug resistant cell.

34. The method of claim 30 wherein the cell comprises a mutation in β-tubulin.

35. The method of claim 30 wherein the cell over produces glutathione.

36. A method for promoting apoptosis in a multidrug resistant cell comprising the steps of contacting a multidrug resistant cell with discodermolide and inducing apoptosis in the cell, wherein the cell is selected from the group consisting of a lung cell, prostate cell, and an epidermoid cell.

37. The method according to claim 36 wherein the multidrug resistant cell is in vitro.

38. The method according to claim 36 wherein the multidrug resistant cell is in vivo.

39. The method of claim 36 wherein the multidrug resistant cell is resistant to paclitaxel.

40. A method for inhibiting the growth of cancer cells having a β-tubulin mutation comprising the steps of contacting at least one cancer cell with a growth inhibiting amount of discodermolide wherein the cell is selected from the group consisting of a lung cell, prostate cell, and an epidermoid cell and wherein the cell comprises a mutation in the protein β-tubulin and inhibiting cell division in the cell.

41. The method according to claim 40 wherein the cell growth is in vitro.

42. The method according to claim 40 wherein the cell growth is in vivo.

43. The method of claim 40 wherein the cell is resistant to paclitaxel.

44. A method for inhibiting growth of a tumor resistant to at least one antineoplastic agent comprising the step of contacting a tumor with discodermolide wherein the tumor comprises cells resistant to at least one antineoplastic agent; wherein the tumor is selected from the group consisting of a lung tumor, prostate tumor, and an epidermoid tumor.

45. The method according to claim 44 wherein the tumor growth is in vitro.

46. The method according to claim 44 wherein the tumor growth is in vivo.

47. The method of claim 44 wherein the cells have a mutation in a β-tubulin protein.

48. The method of claim 44 wherein the cells overproduce glutathione.

49. The method of claim 44 wherein the cells are multidrug resistant.

50. The method of claim 44 wherein the cells comprise raf-1 and wherein raf-1 is phosphorylated in the presence of discodermolide.

51. The method of claim 44 wherein the at least one neoplastic agent is paclitaxel.

\* \* \* \* \*